United States Patent [19]

Waugh et al.

[11] Patent Number: 4,877,743
[45] Date of Patent: Oct. 31, 1989

[54] MONITORING REACTION OF NITROUS OXIDE TO FORM NITROGEN

[75] Inventors: Kenneth C. Waugh, Mere; Godfrey C. Chinchen, Cleveland, both of England

[73] Assignee: Imperial Chemical Industries PLC, London, United Kingdom

[21] Appl. No.: 177,887

[22] Filed: Mar. 31, 1988

Related U.S. Application Data

[63] Continuation of Ser. No. 863,028, May 14, 1986, abandoned.

[30] Foreign Application Priority Data

May 20, 1985 [GB] United Kingdom ............... 8512684

[51] Int. Cl.⁴ .................... G01N 33/00; C01B 21/00
[52] U.S. Cl. .................... 436/116; 436/106; 422/78; 422/80; 423/235; 423/239
[58] Field of Search .............. 423/239, 235; 73/23; 436/34, 37, 113, 114, 116, 106; 422/78, 80

[56] References Cited

U.S. PATENT DOCUMENTS

| | | | |
|---|---|---|---|
| 2,960,870 | 11/1960 | Nelsen et al. | 73/432 |
| 3,843,439 | 10/1974 | Sandler | 204/1 T |
| 3,915,644 | 10/1975 | Walraven | 23/230 R |
| 4,496,249 | 1/1985 | Lee et al. | 374/7 |

FOREIGN PATENT DOCUMENTS

59-69140 4/1984 Japan .

OTHER PUBLICATIONS

"The Measurement of Copper Surface Areas by Reactive Frontal Chromatography", Chinchen et al., *J. of Catalysis*, 103, 79–86, (1987).
Dell et al., "The Adsorption of Oxygen and Other Gases on Copper", Trans. Faraday Soc., 1953, 49, 195–201.
Dell et al., "The Decomposition of Nitrous Oxide on Cuprous Oxide and Other Oxide Catalysts", Trans. Faraday Soc., 1953, 49, 201–209.
Exhibit 1–"Methanol Synthesis Catalysts from Thorium–Copper Intermetallics Preparation and Evalution", Elizabeth G. Baglin, Gary B. Atkinson, and Larry J. Nicks, Ind. Eng. Chem. Prod. Res. Dev. 1981, 20, pp. 87–90.
A Microcalorimetric Method for the Evaluation of Copper Surface Area in Cu–ZnO Catalyst, pp. 443–451, E. Giamello, B. Fubini, P. Lauro and A. Bossi.
Scholten, J. J. F. and Konvalinka, J. A., *Reaction of Nitrous Oxide with Copper Surfaces*, Trans. Faraday Soc., (1969), 65, 2465–73.

*Primary Examiner*—Barry S. Richman
*Assistant Examiner*—T. J. Wallen
*Attorney, Agent, or Firm*—Cushman, Darby & Cushman

[57] ABSTRACT

Methods and apparatus for monitoring the reaction between a metal, and/or metal oxide, reactive with nitrous oxide wherein a mixture of nitrous oxide and a diluent is passed through a bed of a material containing the metal, or metal oxide, and the time to a marked change in the exit gas composition is determined. The procedure is of particular utility for metal surface area determination.

10 Claims, 1 Drawing Sheet

MONITORING REACTION OF NITROUS OXIDE TO FORM NITROGEN

This is a continuation of application Serial No. 863,028, filed May 14, 1986, which was abandoned upon the filing hereof.

BACKGROUND OF THE INVENTION

This invention relates to an oxidation process, and apparatus therefor, and in particular to the reaction of nitrous oxide with metals and metal oxides.

When nitrous oxide is contacted with certain metals, e.g. copper, iron, cobalt, nickel, and silver, or with certain metal oxides that can be oxidised to a higher state, e.g. magnetite, the nitrous oxide is decomposed, oxidising the metal or metal oxide (hereinafter termed the active material) and producing nitrogen (see, for example, Trans. Faraday Soc 65, 1969, pages 2465–73). This reaction occurs only at the surface of the active material and so can be used to determine the surface area of the active material, particularly where the active material has a high surface area, typically above about 1 $m^2.g^{-1}$, as is often the case in materials for use as catalysts.

Heretofore three methods making use of this reaction have been employed for determination of surface areas, viz gravimetric, static, and pulsed flow, techniques.

The gravimetric method simply involves determining the weight of the sample before and after exposure to nitrous oxide. Provided care is taken good accuracy can be achieved. However the technique is time consuming and not suited to routine measurements, e.g. as part of a quality control procedure in catalyst manufacture.

The static method involves leaving the sample in contact with nitrous oxide in a sealed apparatus, then cooling to liquefy the excess of nitrous oxide and measuring the amount of nitrogen produced. This technique again is inconvenient, time consuming, and gives only a moderate accuracy.

The pulsed flow method involves contacting the sample periodically with pulses of a known amount of nitrous oxide and determining the nitrogen/nitrous oxide ratio in the exit gas corresponding to each pulse. Again the technique is inconvenient, time consuming and gives only a poor accuracy: we have found that this technique often gives an accuracy of no better than ±10%.

BRIEF DESCRIPTION OF THE INVENTION

We have now devised a simple, quick, accurate, method, and apparatus suitable therefor, of monitoring the reaction, based on the finding that the reaction is sufficiently rapid to enable a continuous flow, reactive front, analytical technique to be employed.

DETAILED DESCRIPTION OF THE INVENTION

Accordingly we provide a method of monitoring the reaction between nitrous oxide and a material containing at least one metal, and/or metal oxide, that reacts with nitrous oxide comprising passing a mixture of nitrous oxide and an inert diluent other than nitrogen continuously through a bed of the material at a known rate and determining the time interval between (a) the onset of the appearance of nitrogen and (b) the onset of the appearance of nitrous oxide, or the time at which there is a rapid fall of the nitrogen content, in the exit gas.

We also provide apparatus comprising means to pass continuously a mixture of nitrous oxide and an inert diluent at a known rate through a bed of a material containing at least one metal, and/or metal oxide, reactive to nitrous oxide, and means for distinguishing between the presence of nitrogen and the presence of nitrous oxide in the exit gas.

The time interval between the appearance of nitrogen and the appearance of nitrous oxide (or the rapid decline of nitrogen which is virtually coincident with the appearance of nitrous oxide) in the exit gas, multiplied by the proportion of nitrous oxide in the influent gas mixture, multiplied by the flow rate of the influent gas mixture, gives the amount of nitrogen produced. From this, in conjunction with published data, or by reference to calibration using a sample having a known surface area of active material, the surface area of active material can be determined. It is to be noted that no analysis of the exit gas is necessary, although if the method of detection of nitrogen in the exit gas also measures the proportion thereof, this can be used to determine, or as a check on, the proportion of nitrous oxide in the influent gas mixture.

The diluent gas should be inert: helium is a preferred diluent. The flow rate of the diluent/nitrous oxide gas mixture through the sample is preferably constant and is selected, in conjunction with the proportion of nitrous oxide in the gas mixture, to give a convenient time interval, which is preferably in the range 2 to 30 minutes, between the appearance of nitrogen and the appearance of nitrous oxide in the exit gas.

In an alternative, but less preferred, form of the invention the diluent employed is nitrogen. In this case the time interval between commencement of flow of the nitrous oxide containing gas through the sample and the appearance of nitrous oxide in the exit gas is determined. Since the reaction between nitrous oxide and the active material in the sample is relatively rapid, a small correction, based on the flow rate, to this time interval enables the time during which nitrous oxide is reacting to be determined. In some cases sufficiently accurate results may be obtained without the need for such a correction. Measurement of this time interval may also be employed where the diluent is not nitrogen and the detector merely indicates the time from commencement of the flow of the nitrous oxide/diluent gas mixture to the time at which nitrous oxide appears in the exit gas.

The use of a diluent has the advantage that heating of the sample as a result of exothermic reaction between the active material and nitrous oxide is minimised. Such heating, which is liable to occur in techniques, such as the aforementioned gravimetric, static, or pulse flow, methods employing undiluted nitrous oxide, can give rise to over oxidation of the active material, i.e. oxidation of part of the bulk thereof rather than just the surface and hence give rise to errors.

The proportion of nitrous oxide in the nitrous oxide/diluent mixture is preferably in the range 0.5 to 15, particularly 1 to 10, % by volume.

The temperature at which the reaction is effected will depend on the nature of the active material. For metals such as copper, cobalt, iron, nickel, and silver, the bed is preferably maintained at a temperature below about 70° C.: temperatures as low as −80° C. can be used but normally temperatures in the range 0°–60° C. are usefully employed and precise control of the temperature within this range is not normally essential. Oxidic active materials normally require significantly higher temperatures. It has been reported, e.g. in the aforementioned Trans. Faraday Soc. reference, that with copper as the active material, different exposed copper crystal planes have different reactivities. We have found that, at temperatures in the range 20°–60° C. the reaction is so fast that such different activities have no significant effect on the value obtained for the active copper surface area. However if it is desired to assess the proportion of different exposed crystal planes, determination of surface areas at a series of lower temperatures may be performed.

The presence of nitrous oxide and, where the diluent is not nitrogen, the presence of nitrogen, in the exit gas can conveniently be detected by means of a mass spectrometer. Alternatively a katharometer can be employed to detect changes in thermal conductivity given by changes in the exit gas composition and hence to detect the appearances of nitrogen and nitrous oxide respectively.

While the pressure at which the reaction is performed may be at any level, the pressure is conveniently at, or just above, atmospheric, e.g. 1–2 bar absolute.

The apparatus of the invention, particularly for routine or laboratory experimental use, is conveniently automated in known manner.

In many cases it is desirable to ensure that the effects of oxidation of the active material by exposure to the air, e.g. during charging of the sample to the apparatus, are eliminated. Thus it is often desirable to subject the sample to an appropriate reduction procedure prior to effecting the reaction with nitrous oxide. Normally reduction can be achieved by passing a gas comprising a reducing agent, such as hydrogen or carbon monoxide, preferably in admixture with an inert diluent such as helium or nitrogen, through the sample bed at a temperature, and for a time, sufficient to effect the required reduction. In a preferred form of the invention, where the apparatus is automated, this reduction step may also be programmed into the operation of the apparatus. In that case the latter will normally include means for heating the sample bed to the required reduction temperature and means for passing a reducing agent through the bed prior to passage of the nitrous oxide/diluent mixture therethrough. Between reduction and passage of the nitrous oxide/diluent mixture, the sample is preferably purged with an inert gas, e.g. to remove any residual reducing agent, and, where the latter was employed in admixture with nitrogen and the diluent in the nitrous oxide/diluent gas mixture is not nitrogen, any residual nitrogen.

The sample bed should be in such a form that the influent nitrous oxide/diluent gas mixture flows therethrough in a substantially plug flow manner with no significant route for the influent gas to by-pass the bed. To ensure essentially plug flow, the ratio of the length of the sample bed to the maximum cross-sectional dimension thereof is preferably at least 1, and in particular is at least 2. To avoid significant by-pass of the bed, the latter should occupy essentially the whole cross-sectional area of the vessel through which the gas mixture is passed. While in some cases the sample may be in the form of, for example, a single pellet within a close fitting tube, it is preferred that the bed comprises a plurality of particles of the sample, which may comprise the active material in admixture with particles of a diluent material such as alumina, having a maximum dimension that is less than about one third of the minimum cross-sectional dimension of the vessel.

Since there is often a shrinkage of the bed as a result of a reduction step, to ensure adequate packing of the sample bed to minimise by-passing of the bed by the nitrous oxide/diluent gas mixture where such a reduction step is employed, the bed is preferably disposed in an elongated vessel, e.g. a tube, having its longitudinal axis vertical.

The technique of the present invention may be used not only on a small laboratory scale but also for the assessment of the surface area of active material in a bed employed in a production process: for example, since the activity of a catalyst often depends on the surface area of active material, and this surface area often decreases after a catalyst has been in use for some time, e.g. as a result of sintering and/or poisoning, by measurement of the surface area of active catalyst in a plant catalytic reactor, an indication can be given of the residual activity of the catalyst and hence an estimate made of its useful life.

This method of assessing catalytic activity can also be used in the laboratory for comparison of different catalysts and/or the effect of changing process conditions on the rate of catalytic activity decline.

Another use of the invention is to monitor processes wherein an active material is surface oxidised to a predetermined extent: thus it is often desirable to surface oxidise catalytically active metals to passivate them prior to transport and charging to a catalytic reactor wherein the surface oxidised metal is subsequently reduced to active metal. The present invention can be used to determine whether all the active material has been passivated.

BRIEF DESCRIPTION OF THE DRAWINGS

The invention is illustrated by reference to the accompanying drawings wherein.

DETAILED DESCRIPTION OF THE DRAWINGS

Figure 1:
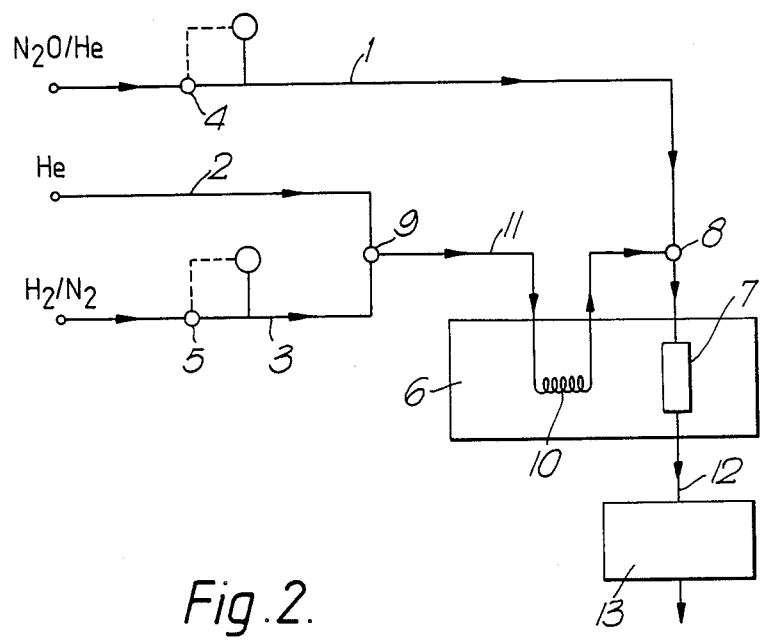
FIG. 1 is a line diagram of the apparatus.

The apparatus comprises three gas inlet lines 1, 2, 3 fitted with reducing valves (not shown) to supply gases at a pressure of just above 1 bar absolute. Gas lines 1, 2 and 3 were connected to supplies of a nitrous oxide/helium mixture (reaction gas), helium (purge gas), and a hydrogen/nitrogen mixture (reduction gas) respectively. Valve coupled flow meters 4, 5 are provided to control, and measure, the rate of gas flow through lines 1 and 3 respectively. The apparatus further includes an oven 6 in which a vertically mounted reaction tube 7 containing the sample to be investigated is located. The gas supply to the reaction tube can be selected by valves 8 and 9. An oxygen removal column 10, situated in oven 6, is provided in the line 11 between valves 8 and 9 to remove any residual oxygen from the purge gas. The column 10 is positoned between valves 8 and 9, rather than in line 2 before valve 9, so that the reduction gas is passed through the column 10 to regenerate the latter during the reduction step. Likewise column 10 is positioned upstream of valve 8 because otherwise nitrous oxide would be absorbed by column 10. The exit gas from reactor tube 7 is fed, via line 12, to a detector 13 e.g. a katharometer and/or a mass spectrometer.

Oxygen removal, i.e. by column 10, from the purge gas is desirable to avoid oxidation of the active material by oxygen present as an impurity in the purge gas which is used to purge reactor tube 7 after the reduction step. Provided the reaction gas has a relatively low oxygen content, e.g. below 10 ppm (by volume), no oxygen removal stage is generally required in the reaction gas line 1 because the amount of oxidation by that residual oxygen will generally be negligible in comparison to that effected by the nitrous oxide.

The reactor tube 7 employed had an internal diameter of about 6 mm and was charged with a weighted quantity of the sample that had been pulverised to a particle size below about 1 mm. The sample quantity employed was sufficient to give about 5-6 cm length in tube 7. The sample bed was retained in tube 7 by means of a plug of quartz wool at the base (outlet end) of tube 7. The tube 7, after charging the sample thereto, was purged of air by means of purge gas from line 2 and then the feed to tube 7 switched to the reduction gas (which contained about 5% by volume hydrogen) from line 3. The oven temperature was then increased at a controlled rate to the desired reduction temperature and, after a predetermined time at that temperature, cooled to the desired reaction temperature.

The gas feed was then switched to line 2 to purge the reactor tube 7 of residual hydrogen and nitrogen. Then valve 8 was switched to introduce the reaction gas. The appearance of nitrogen in the exit gas, as detected by detector 13, occurred shortly after switching valve 8. The proportion of nitrogen in the exit gas rose rapidly to a peak and remained constant, or declined slightly, for a period of time, and then dropped rapidly. At the same time as the nitrogen content dropped rapidly, nitrous oxide appeared in the exit gas. The time interval between the appearance of nitrogen in the exit gas and the rapid fall in the nitrogen content thereof was measured and then valve 8 switched to allow the purge gas from line 2 to purge the system.

Figure 2:
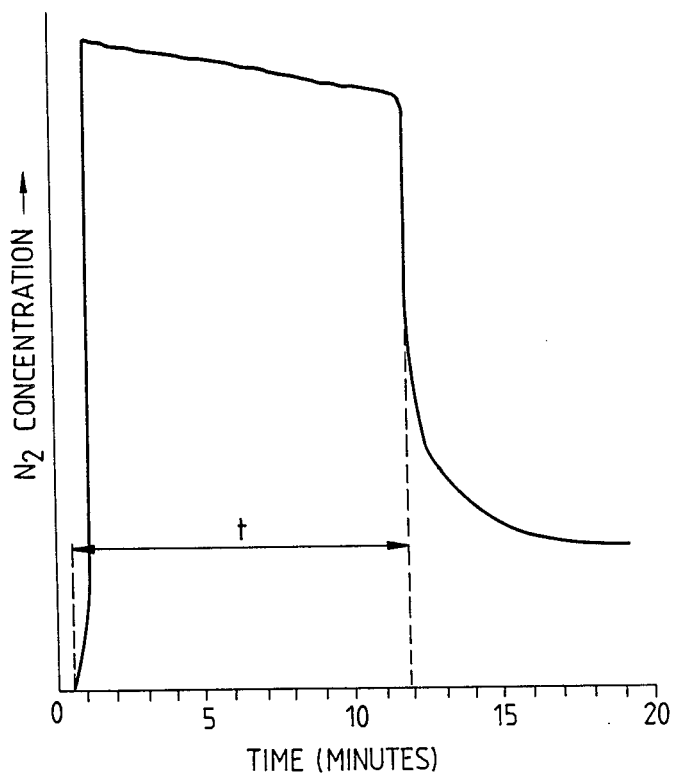
FIG. 2 is a trace given by the nitrogen detector employed in the apparatus.

In a specific example 2.285 g of a pulverised copper/zinc oxide/alumina catalyst was employed as the sample giving a bed of 5.5 cm length. The reduction gas flow rate was 2.5 cm$^3$.s$^{-1}$, (at NTP). The reactor tube 7 was heated from ambient temperature to 230° C. at a rate of 0.13° C.s$^{-1}$, held at 230° C. for 2 hours and then allowed to cool to 50° C. Using a reaction gas containing 2.45% by volume of nitrous oxide at a rate of 0.91 cm$^3$.s$^{-1}$ (at NTP) and a mass spectrometer to monitor the exit gas for nitrogen, the trace shown in FIG. 2 was obtained. In this trace switching of valve 8 occurred at zero time. Nitrogen was first detected about 30 seconds after switching valve 8 and reached a peak about a further 30 seconds. During the next 10½ minutes the trace showed a slow decline in nitrogen content and then dropped rapidly to a residual level (which arose as a result of some decomposition of nitrous oxide in the mass spectrometer). The time interval (t) between the onset of the appearance of nitrogen and the start of the rapid decline in nitrogen content was 11.2 minutes.

Calculation showed that the volume of nitrogen produced by the reaction in time t was 14.9 cm$^3$ (at NTP) from which it was calculated that the copper surface area of the catalyst was 32.7 m$^2$.g$^{-1}$ using the assumption that there were 0.5×10$^{15}$ oxygen atoms per cm$^2$ of copper surface by virtue of the reaction

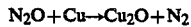

$$N_2O + Cu \rightarrow Cu_2O + N_2$$

giving a half monolayer coverage of the copper by oxygen.

A similar result was obtained in a repeat determination on another sample of the catalyst using a katharometer as the detector. Repeat determinations showed that the reproducibility was about +2%.

The results correlated well with those given by a gravimetric technique.

By simple modification of the apparatus it is possible to have several reaction tubes 7 in parallel with appropriate valves so that the samples therein can be reduced at the same time under identical conditions and then subjected to the reaction gas in sequence.

We claim:

1. A method of monitoring the reaction between nitrous oxide and a material containing at least one reactive constituent selected from the group consisting of a metal and a metal oxide, said reactive constituent being reactive with nitrous oxide to form nitrogen, comprising
    (i) commencing, and thereafter continuing, flow of a mixture of nitrous oxide and an inert diluent, other than nitrogen, of a known and constant composition, through a bed of the material at a known rate, so that all of said mixture passes through the bed, the proportion of nitrous oxide in said mixture, and the rate of flow thereof, in relation to the amount of said material, being such that for a period of time all the nitrous oxide in the mixture reacts with the material so that there is nitrogen, but not nitrous oxide, in the exit gas leaving the bed, and
    (ii) determining the time interval between
        (a) the onset of the appearance of nitrogen in the exit gas and
        (b) the onset of the appearance of nitrous oxide, or the time at which there is a rapid fall in nitrogen content, in the exit gas.

2. A method according to claim 1 wherein the nitrous oxide/diluent gas mixture contains 0.5 to 15% v/v of nitrous oxide.

3. A method according to claim 1 wherein the material contains at least one metal selected from the class consisting of copper, cobalt, iron, nickel, and silver and the bed is maintained at a temperature below 70° C.

4. A method according to claim 1 wherein, prior to commencement of the passage of the nitrous oxide/diluent mixture, a gas comprising a reducing agent is passed through the bed, and then the bed is purged with an inert gas.

5. A process according to claim 1 where the proportion of nitrous oxide in the nitrous oxide/diluent mixture and the flow rate thereof is such, in relation to the amount of said material, that the period of time during which all the nitrous oxide in the mixture reacts with the material so that there is nitrogen, but no nitrous oxide, in the exit gas leaving said bed, is of 2 to 30 minutes duration.

6. A method of monitoring the reaction between nitrous oxide and a material containing at least one reactive constituent selected from the group consisting of a metal and a metal oxide, said reactive constituent being reactive with nitrous oxide to form nitrogen, comprising
    (i) commencing, and thereafter continuing, flow of a mixture of nitrous oxide and an inert diluent, other than nitrogen, of a known and constant composition, through a bed of the material at a known rate, so that all of said mixture passes through the bed, the proportion of nitrous oxide in said mixture, and the rate of flow thereof, in relation to the amount of said material, being such that for a period of time all the nitrous oxide in the mixture reacts with the material so that there is nitrogen, but no nitrous oxide, in the exit gas leaving the bed, and (ii) determining the time interval between
 (a) the commencement of flow of the mixture and
 (b) the appearance of nitrous oxide in the exit gas.

7. Oxidation reaction apparatus comprising:

a vessel adapted to contain a sample of a material containing at least one reactive constituent selected from the group consisting of a metal, and a metal oxide, said reactive constituent being reactive with nitrous oxide to form nitrogen, said vessel being provided with an inlet and an outlet positioned such that all of a gas flowing from said inlet to said outlet passes through said sample;

first supply means to supply an inert diluent purge gas to said inlet;

second supply means to supply a mixture of nitrous oxide and an inert diluent gas to said inlet;

monitoring means to continuously monitor the gas from said outlet, said monitoring means being capable of distinguishing between the presence of nitrogen and the presence of nitrous oxide in the gas from said outlet;

means to switch from said first supply means to said second supply means;

control and monitoring means to maintain the flow of said mixture of nitrous oxide and an inert diluent gas at a known constant rate from said second supply means to said inlet of said vessel; and means to determine the length of the period, after switching from said first supply means to said second supply means, during which there is no nitrous oxide in said gas from said outlet.

8. Apparatus according to claim 7 wherein said means for distinguishing between the presence of nitrogen and the presence of nitrous oxide is a mass spectrometer or a katharometer.

9. Apparatus according to claim 7 including means to remove oxygen present as an impurity from at least the purge gas.

10. Apparatus as claimed in claim 7 including third supply means to supply a gas containing a reducing agent continuously to said inlet and switching means to switch from said third supply means to said first supply means.

* * * * *